United States Patent
Washizu (10) Patent No.: US 11,181,504 B2
(45) Date of Patent: Nov. 23, 2021

(54) MEASUREMENT APPARATUS

(71) Applicant: ADVANTEST CORPORATION, Tokyo (JP)

(72) Inventor: Nobuei Washizu, Tokyo (JP)

(73) Assignee: ADVANTEST CORPORATION, Tokyo (JP)

( * ) Notice: Subject to any disclaimer, the term of this patent is extended or adjusted under 35 U.S.C. 154(b) by 252 days.

(21) Appl. No.: 16/296,790

(22) Filed: Mar. 8, 2019

(65) Prior Publication Data

US 2020/0033292 A1 Jan. 30, 2020

(30) Foreign Application Priority Data

Jul. 26, 2018 (JP) .............................. JP2018-140616

(51) Int. Cl.
*G01R 19/00* (2006.01)
*G01R 27/02* (2006.01)
*H03F 1/42* (2006.01)
*G01N 27/447* (2006.01)
*G01N 33/487* (2006.01)

(52) U.S. Cl.
CPC . *G01N 27/44791* (2013.01); *G01N 33/48721* (2013.01); *G01R 19/00* (2013.01)

(58) Field of Classification Search
CPC ....... G01N 27/44791; G01N 33/48721; G01R 19/00
See application file for complete search history.

(56) References Cited

U.S. PATENT DOCUMENTS

| 2005/0178974 A1* | 8/2005 | Sobek ............... H01J 49/165 250/423 R |
| 2013/0048499 A1 | 2/2013 | Mayer et al. |
| 2016/0154033 A1* | 6/2016 | Kuramochi ........ G01R 19/0053 324/120 |

FOREIGN PATENT DOCUMENTS

| DE | 2534955 A1 | 2/1976 |
| DE | 102006032906 A1 | 2/2007 |
| GB | 193393 | 10/1923 |
| JP | H0440373 A | 2/1992 |
| JP | H07504989 A | 6/1995 |
| JP | 2004510980 A | 4/2004 |
| JP | 2011513739 A | 4/2011 |

OTHER PUBLICATIONS

German Office Action for corresponding DE Application No. 102019116347.1; dated, Aug. 3, 2021.

* cited by examiner

*Primary Examiner* — Clayton E. LaBalle
*Assistant Examiner* — Michael A Harrison
(74) *Attorney, Agent, or Firm* — Cantor Colburn LLP (57) ABSTRACT

A nanopore device measures a current signal Is that flows through the nanopore device, which has an aperture and an electrode pair. A transimpedance amplifier converts the current signal Is into a voltage signal Vs. A voltage source is configured to apply a DC bias voltage Vb across the electrode pair in a normal measurement mode, and to apply a calibration voltage Vcal across the electrode pair in a calibration mode. In the calibration mode, at least one circuit constant of a measurement apparatus is calibrated based on the output signal Vs of the transimpedance amplifier and the calibration voltage Vcal.

13 Claims, 6 Drawing Sheets

MEASUREMENT APPARATUS

CROSS REFERENCE TO RELATED APPLICATIONS

The present application claims priority under 35 U.S.C. § 119 to Japanese Patent Application No. 2018-140616, filed on Jul. 26, 2018 is incorporated herein by reference in its entirety.

BACKGROUND OF THE INVENTION

1. Field of the Invention

The present invention relates to measurement employing a nanopore device.

2. Description of the Related Art

A particle size distribution measurement method, which is referred to as the "electrical sensing zone method (the Coulter principle)", is known. With this measurement method, an electrolyte solution including particles is applied such that it passes through an aperture that is referred to as a "nanopore". When a particle passes through such an aperture, the amount of the electrolyte solution with which the aperture is filled is reduced by an amount that corresponds to the volume of the particle, which raises the electrical resistance of the aperture. Accordingly, in a case in which the aperture has a thickness that is larger than the particle size, by measuring the electrical resistance of the aperture, this arrangement is capable of measuring the volume of the particle that passes through the aperture. Conversely, in a case in which the aperture has a thickness that is sufficiently smaller than the particle size, this arrangement is capable of measuring the cross-sectional area (i.e., diameter) of the particle that passes through the aperture.

Figure 1:
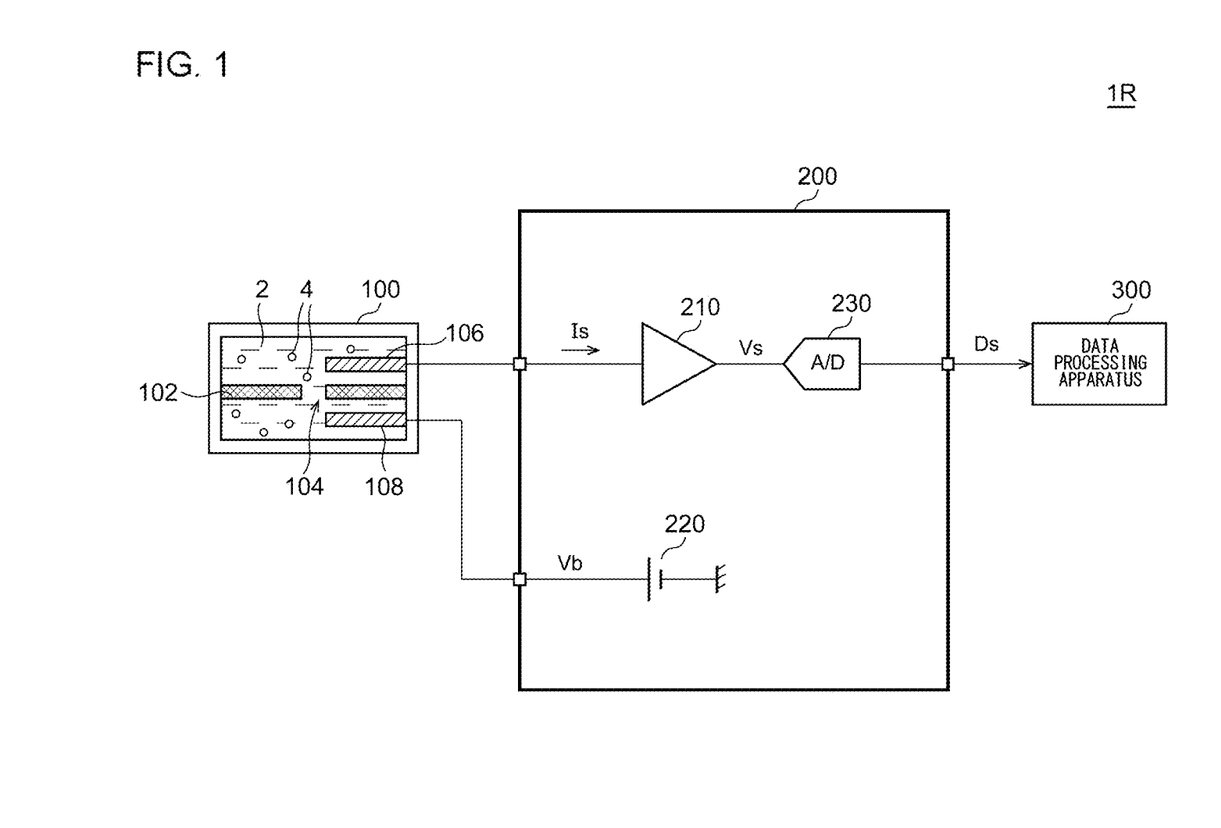
FIG. 1 is a block diagram showing a microparticle measurement system employing the electrical sensing zone method.

FIG. 1 is a block diagram showing a microparticle measurement system 1R employing the electrical sensing zone method. The microparticle measurement system 1R includes a nanopore device 100, a measurement apparatus 200R, and a data processing apparatus 300.

The internal space of the nanopore device 100 is filled with an electrolyte solution 2 including particles 4 to be detected. The internal space of the nanopore device 100 is partitioned by a nanopore chip 102 so as to define two internal spaces. Electrodes 106 and 108 are provided to the two spaces. When an electric potential difference is generated between the electrodes 106 and 108, this generates a flow of ion current between the electrodes. Furthermore, the particles 4 migrate by electrophoresis from a given space to the other space via the aperture 104.

The measurement apparatus 200R generates the electric potential difference between the electrode pair 106 and 108, and acquires information having a correlation with the resistance value Rp between the electrode pair. The measurement apparatus 200R includes a transimpedance amplifier 210, a voltage source 220, and a digitizer 230. The voltage source 220 generates an electric potential difference Vb between the electrode pair 106 and 108. The electric potential difference Vb functions as a driving source of the electrophoresis, and is used as a bias signal for measuring the resistance value Rp.

A microscopic current Is flows between the electrode pair 106 and 108 in inverse proportion to the resistance of the aperture 104.

$$Is = Vb/Rp \quad (1)$$

The transimpedance amplifier 210 converts the microscopic current Is into a voltage signal Vs. With the conversion gain as r, the following expression holds true.

$$Vs = r \times Is \quad (2)$$

By substituting Expression (1) into Expression (2), the following Expression (3) is obtained.

$$Vs = Vb \times r/Rp \quad (3)$$

The digitizer 230 converts the voltage signal Vs into digital data Ds. As described above, the measurement apparatus 200R is capable of acquiring the voltage signal Vs in inverse proportion to the resistance value Rp of the aperture 104.

Figure 2:
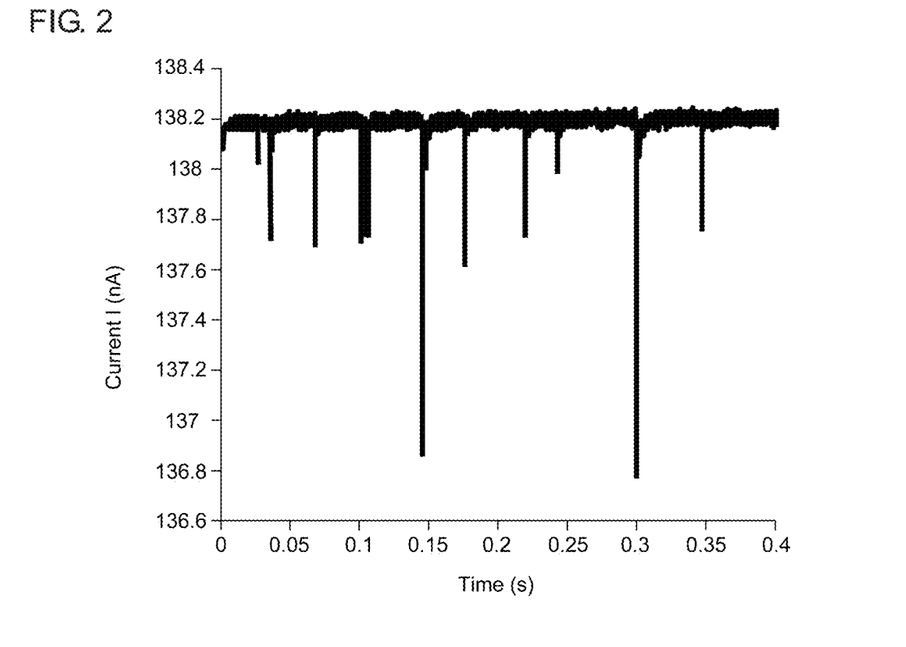
FIG. 2 is a waveform diagram showing an example of a microscopic current is measured by a measurement apparatus.

FIG. 2 is a waveform diagram of an example of the microscopic current Is measured by the measurement apparatus 200R. It should be noted that the vertical axis and the horizontal axis shown in the waveform diagrams and the time charts in the present specification are expanded or reduced as appropriate for ease of understanding. Also, each waveform shown in the drawing is simplified or exaggerated for emphasis or ease of understanding.

During a short period of time in which a particle passes through the aperture 104, the resistance value Rp of the aperture 104 becomes large. Accordingly, the current Is drops in the form of a pulse every time a particle passes through the aperture 104. The change in the current Is has a correlation with the particle size. The data processing apparatus 300 processes the digital data Ds so as to analyze the number of the particles 4 contained in the electrolyte solution 2, the particle distribution thereof, or the like.

RELATED ART DOCUMENTS

Patent Documents

[Patent document 1]
  Japanese Patent Application Laid Open No. 2011-513739
[Patent document 2]
  Japanese Patent Application Laid Open No. H04-040373
[Patent document 3]
  PCT Japanese Translation Patent Publication No. H07-504989
[Patent document 4]
  Japanese Patent Application Laid Open No. 2004-510980

With conventional electrical sensing zone methods, measurement is made beforehand for standard particles for calibration each having a known particle size (volume), so as to acquire a correlation between the particle size of each standard particle and the digital data Ds. Subsequently, measurement is made for particles each having an arbitrary particle size so as to acquire the digital data Ds. Furthermore, the particle sizes are acquired based on the correlation obtained beforehand. Accordingly, the information obtained using such conventional electrical sensing zone methods is limited to the number of particles or otherwise the particle size (volume). That is to say, this arrangement is not capable of acquiring detailed characteristic information such as the particle shape or the like.

SUMMARY OF THE INVENTION

With respect to the cause of the problem, the present inventor directs attention to the response speed (bandwidth) of the microparticle measurement system 1. That is to say, in a case in which the microparticle measurement system 1 operates at a sufficiently high speed, the waveform of the digital data Ds has a correlation with the particle shape. However, for the reason noted below, it is difficult to provide such a conventional microparticle measurement system 1 with a broad bandwidth.

Figure 3:
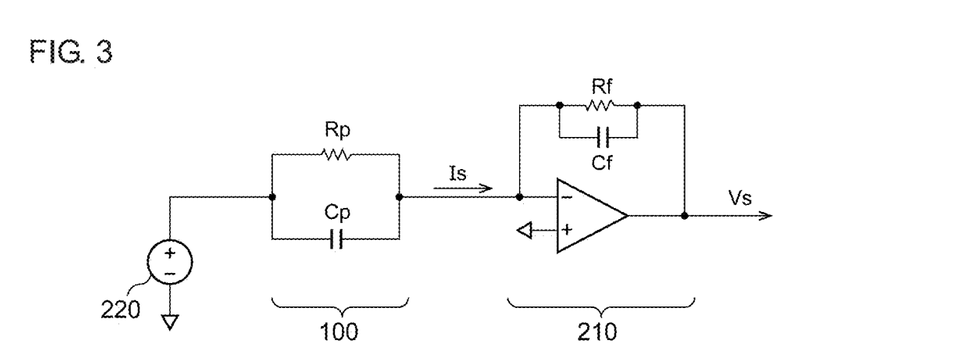
FIG. 3 is an equivalent circuit diagram showing a nanopore device and a transimpedance amplifier.

FIG. 3 is an equivalent circuit diagram showing the nanopore device 100 and the transimpedance amplifier 210.

As the diameter of the aperture 104 becomes smaller, the resistance value Rp of the aperture 104 becomes larger, and measurement in a micro current range becomes necessary. In order to provide a S/N ratio that satisfies the requirements, a resistor Rf having a resistance value of 100 MΩ to 1 GΩ is required. In this case, the resistor Rf is mounted as a high-precision lead resistor for a measurement device or otherwise a chip resistor. However, such a resistor involves a non-negligible parasitic capacitance Cf on the order of several hundred fF. This parasitic capacitance Cf drastically narrows the bandwidth of the amplifier (on the order of several kHz to several dozen kHz). This leads to difficulty in acquiring the waveform information for acquiring detailed characteristic values with respect to the particle 4.

The nanopore device 100 is represented by an equivalent circuit including a resistance value Rp of the aperture 104 and the parasitic capacitance Cp coupled in parallel. With the parasitic capacitance Cp, overshoot or undershoot of the output waveform of the voltage Vs occurs, which degrades the stability of the transimpedance amplifier 210. In order to improve the waveform, the transimpedance amplifier 210 side is designed such that the product (Rf*Cf) thereof matches the product (Rp×Cp) of the nanopore device 100 side. This means that it is necessary to further increase the parasitic capacitance Cf. That is to say, there is a tradeoff relation between the bandwidth of the transimpedance amplifier 210 and the stability thereof.

Furthermore, Rp and Cp change due to individual variation of the nanopore device 100 and manual application of a reagent. This leads to a problem of an unstable output waveform.

The present invention has been made in view of such a situation. Accordingly, it is an exemplary purpose of an embodiment of the present invention to provide a measurement apparatus that is capable of accurately measuring the current waveform.

An embodiment of the present invention relates to a measurement apparatus structured to measure a current signal that flows through a nanopore device having an aperture and an electrode pair. The measurement apparatus comprises: a transimpedance amplifier structured to convert the current signal into a voltage signal; and a voltage source structured to apply a DC bias voltage across the electrode pair in a normal measurement operation mode, and to apply a calibration voltage including an AC component across the electrode pair in a calibration mode. The measurement apparatus is configured to be capable of calibrating at least one circuit constant of the measurement apparatus based on an output signal of the transimpedance amplifier and the calibration voltage in the calibration mode.

It is to be noted that any arbitrary combination or rearrangement of the above-described structural components and so forth is effective as and encompassed by the present embodiments. Moreover, this summary of the invention does not necessarily describe all necessary features so that the invention may also be a sub-combination of these described features.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which.

DETAILED DESCRIPTION OF THE INVENTION

The invention will now be described based on preferred embodiments which do not intend to limit the scope of the present invention but exemplify the invention. All of the features and the combinations thereof described in the embodiment are not necessarily essential to the invention.

In the present specification, the state represented by the phrase "the member A is coupled to the member B" includes a state in which the member A is indirectly coupled to the member B via another member that does not substantially affect the electric connection between them, or that does not damage the functions or effects of the connection between them, in addition to a state in which they are physically and directly coupled.

Similarly, the state represented by the phrase "the member C is provided between the member A and the member B" includes a state in which the member A is indirectly coupled to the member C, or the member B is indirectly coupled to the member C via another member that does not substantially affect the electric connection between them, or that does not damage the functions or effects of the connection between them, in addition to a state in which they are directly coupled.

Basic Configuration

Figure 4:
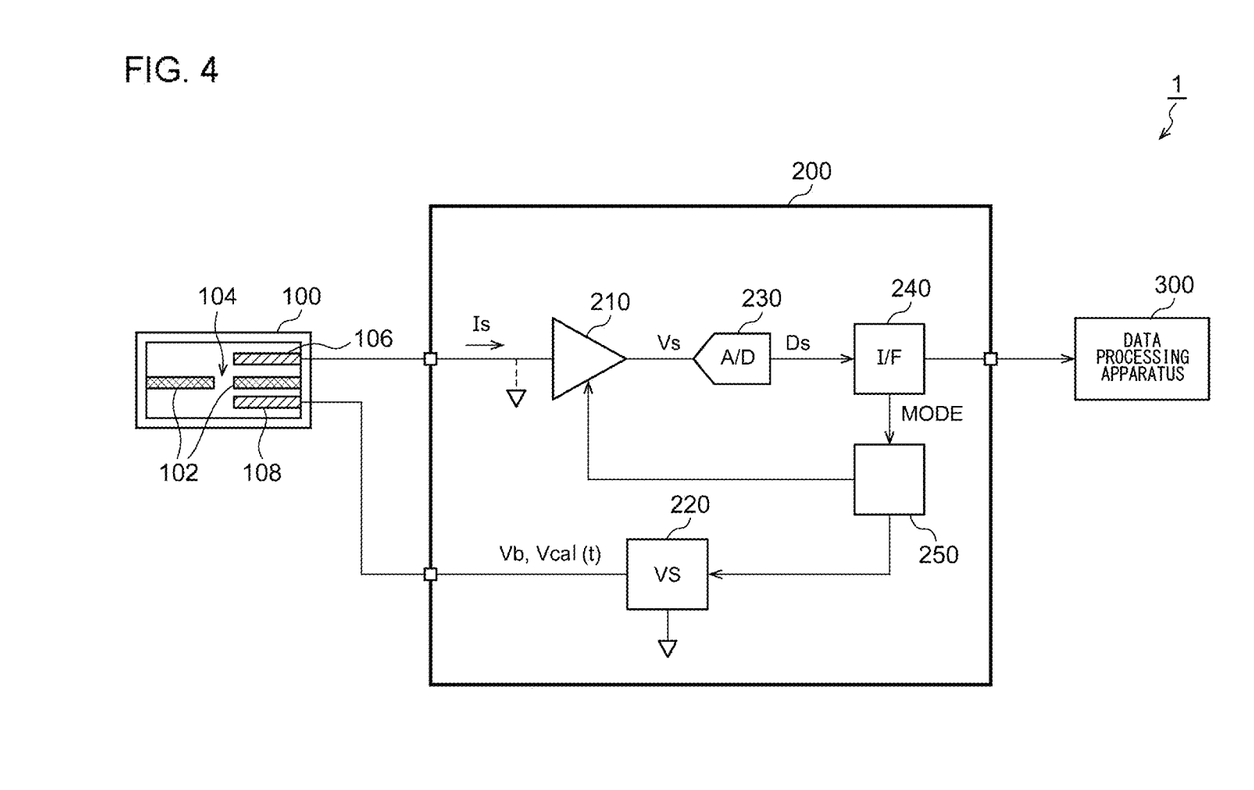
FIG. 4 is a block diagram showing a microparticle measurement system according to an embodiment.

FIG. 4 is a block diagram showing a microparticle measurement system 1 according to an embodiment. The microparticle measurement system 1 includes a nanopore device 100, a measurement apparatus 200, and a data processing apparatus 300.

The nanopore device 100 is configured as described with reference to FIG. 1. Specifically, the nanopore device 100 includes a nanopore chip 102 provided with an aperture 104, and an electrode pair 106 and 108. The internal space of the nanopore chip 102 is filled with an electrolyte solution such as a KCl (potassium chloride) solution, PBS (phosphate buffered saline) solution, or the like.

The measurement apparatus 200 is configured to apply a voltage across the electrode pair 106 and 108, and to measure the current Is that flows through the aperture 104. The measurement apparatus 200 includes a transimpedance amplifier 210, a voltage source 220, a digitizer 230, an interface 240, and a calibration controller 250.

The data processing apparatus 300 functions as a user interface. Furthermore, the data processing apparatus 300 integrally controls the overall operation of the microparticle measurement system 1, and has functions of acquiring, storing, and displaying the measurement results. The data processing apparatus 300 may be configured as a general-purpose computer or workstation. Also, the data processing apparatus 300 may be configured as a dedicated hardware component designed for the microparticle measurement system 1.

The measurement apparatus 200 is switchable between a normal measurement mode and a calibration mode. The data processing apparatus 300 switches the operation mode of the measurement apparatus 200 according to the operation of the user (operator).

The operation in the normal measurement mode is the same as that of the measurement apparatus 200R shown in FIG. 1. In the normal measurement mode, the voltage source 220 applies a DC bias voltage Vb across the electrode pair 106 and 108. The transimpedance amplifier 210 converts the current Is that flows through the nanopore device 100 into a voltage signal Vs. The digitizer 230 converts the voltage signal Vs into digital data Ds. The interface 240 transmits the digital data Ds to the data processing apparatus 300. The time-series data of the digital data Ds represents the current waveform. The data processing apparatus 300 processes the digital data Ds acquired in the normal measurement mode, so as to acquire the number of the particles 4 contained in the electrolyte solution 2 and the particle sizes thereof. Furthermore, in a case of employing the calibration mode described below so as to raise the precision of the measurement of the current waveform, the data processing apparatus 300 is capable of acquiring detailed characteristic values such as the shape of each particle based on the current waveform.

Next, description will be made regarding the calibration mode. When the interface 240 receives predetermined control data from the data processing apparatus 300, the measurement apparatus 200 is set to the calibration mode. In the calibration mode, the calibration controller 250 controls the operation of the measurement apparatus 200.

The calibration controller 250 instructs the voltage source 220 to generate a voltage signal for calibration use. Specifically, the voltage source 220 is configured to apply a calibration voltage Vcal including an AC component across the electrode pair 106 and 108.

For example, the input terminal of the transimpedance amplifier 210, i.e., the electrode 106, is virtually grounded. By applying the calibration voltage Vcal including an AC component to the electrode 108, the electric potential difference between the two electrodes is changed. The waveform of the calibration voltage Vcal is represented by Vcal(t).

In the calibration mode, the internal space of the nanopore device 100 is filled with the electrolyte solution 2 containing no particles 4. Accordingly, the resistance value Rp across the electrode pair 106 and 108 is constant. Accordingly, the voltage signal Vs(t) occurs at the output terminal of the transimpedance amplifier 210 according to the waveform Vcal(t) of the calibration voltage Vcal.

The measurement apparatus 200 is configured to correct at least one circuit constant based on a relation between the output signal Vs of the transimpedance amplifier 210 and the calibration voltage Vcal. Next, description will be made regarding an operation for optimizing the circuit constant.

The transfer function that represents the transfer from the output of the voltage source 220 up to an output node of the transimpedance amplifier 210 is represented by H(s). With the spectrum of the voltage signal Vs(t) as $vs(\omega)$, and with the spectrum of the calibration voltage Vcal(t) as $vcal(\omega)$, the following Expression holds true.

$$vs(\omega) = H(\omega) \times vcal(\omega)$$

The change of the circuit constant of the measurement apparatus 200 is equivalent to the change of the transfer function $H(\omega)$. Accordingly, from the viewpoint of the frequency domain, the circuit constant may preferably be optimized such that the spectrum $vs(\omega)$ of the measured voltage signal Vs approaches the spectrum $vcal(\omega)$ of the calibration voltage Vcal.

From the viewpoint of the time domain, the circuit constant may preferably be optimized such that the time waveform Vs(t) of the measured voltage signal Vs approaches the time waveform Vcal(t) of the calibration voltage Vcal.

The data processing apparatus 300 may support a calibration operation including the optimization of the circuit constant. For example, the data processing apparatus 300 may generate waveform data Dcal of the calibration voltage Vcal(t), and may transmit the waveform data Dcal to the interface 240. The voltage source 220 may convert the waveform data received by the calibration controller 250 into the analog calibration voltage Vs(t). The data processing apparatus 300 may change the circuit constant such that the digital data Ds that represents the waveform of the voltage signal Vs matches the waveform of the waveform data Dcal.

Alternatively, the data processing apparatus 300 may convert the digital data Ds and the waveform data DCAL into frequency domain data by means of a Fourier transform, and may change the circuit constants such that they approach each other in the frequency domain.

Alternatively, the data processing apparatus 300 may convert the digital data Ds and the waveform data Dcal into frequency domain data by means of a Fourier transform, and may calculate the ratio between them, which is employed as the transfer function H(s). Furthermore, the data processing apparatus 300 may adjust the circuit constant such that the transfer function H(s) thus calculated approaches ideal characteristics.

Also, the operator may manually support a part of the operation for optimizing the circuit constant. For example, the data processing apparatus 300 may display the waveform of the calibration voltage and the waveform (or otherwise spectrum) of the measured voltage signal on a display such that they can be compared. The operator may visually compare the two waveforms (spectrums), and may select the circuit constant such that they approach each other.

It should be noted that the calibration operation may be executed by the calibration controller 250 instead of the data processing apparatus 300, or otherwise may be shared by the data processing apparatus 300 and the calibration controller 250.

Figure 5A:
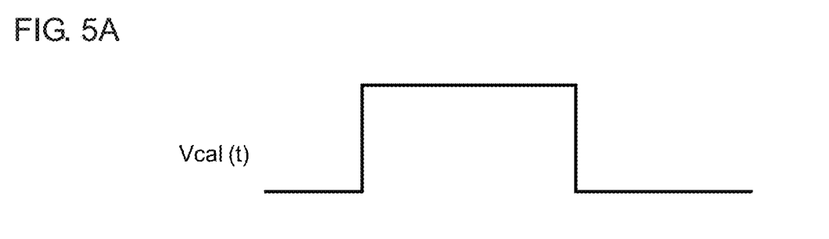
FIG. 5A and FIG. 5B are diagrams showing an example of a calibration operation.
Figure 5B:
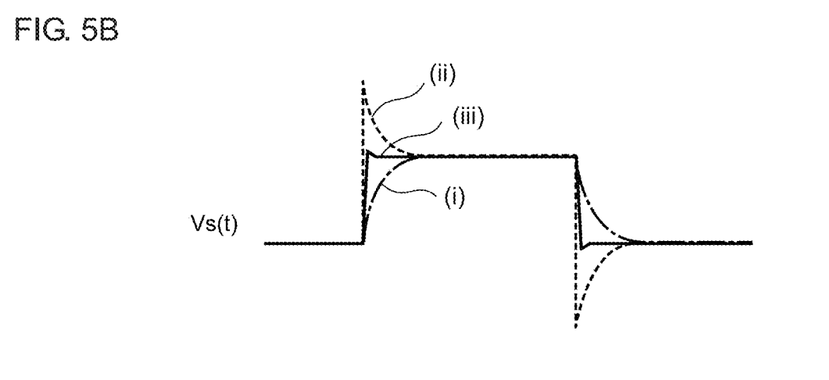

The above is the configuration of the microparticle measurement system 1. FIG. 5A and FIG. 5B are diagrams showing an example of the calibration operation. In this example, a rectangular wave is employed as the calibration voltage Vs(t). FIG. 5A and FIG. 5B show the waveform Vs(t) of the voltage signal that changes according to a change of the circuit constant of the measurement apparatus 200. The waveform (i) represents a state in which the response speed is low, i.e., a narrow bandwidth state. Conversely, the waveform (ii) represents a state in which, although the response speed is high due to a high gain of the high-frequency components, oscillation readily occurs due to its small phase margin. By optimizing the circuit constant, as represented by the waveform (iii), this arrangement is capable of supporting both high-speed operation and stability.

The microparticle measurement system 1 that can be optimized in the calibration mode has an additional advantage as described below. With conventional techniques, there is large distortion in the waveform of the voltage signal Vs. This leads to a difficulty in extracting the information (characteristic values) with respect to the shape of each particle 4. In contrast, with the microparticle measurement system 1 according to the embodiment, the voltage signal Vs is provided with reduced waveform distortion. Accordingly, the voltage waveform has a strong correlation with the particle diameter distribution in the particle height direction. Accordingly, the microparticle measurement system 1 is capable of extracting the information (characteristic values) with respect to the shape of each particle 4.

With the microparticle measurement system 1 according to the embodiment, this arrangement is capable of canceling out the effects of variation of the resistance Rp that occurs due to manufacturing variation of the nanopore device 100 or due to variation of application of a reagent. Furthermore, this arrangement is capable of canceling out the effects of variation of the capacitance Cp that occurs due to manufacturing variation of the nanopore device 100.

Furthermore, this arrangement allows the same measurement apparatus 200 to support measurement for multiple nanopore devices 100 configured with different design values of the diameter of the aperture 104, and with different design values of the distance between the electrode pair 106 and 108.

The present invention encompasses various kinds of apparatuses and methods that can be regarded as a block configuration or a circuit configuration shown in FIG. 4, or otherwise that can be derived from the aforementioned description. That is to say, the present invention is not restricted to a specific configuration. More specific description will be made below regarding example configurations and embodiments for clarification and ease of understanding of the essence of the present invention and the operation. That is to say, the following description will by no means be intended to restrict the technical scope of the present invention.

Figure 6:
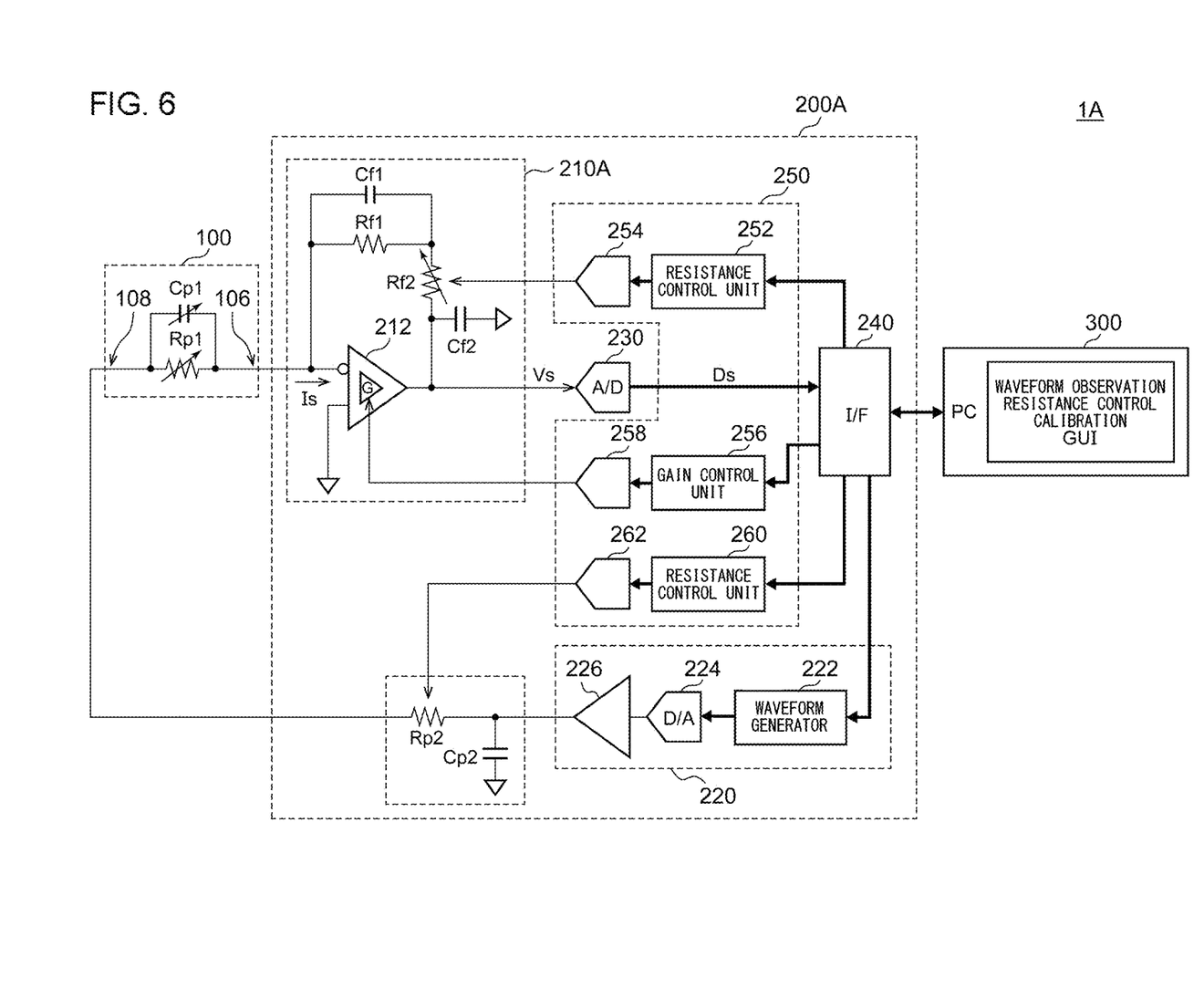
FIG. 6 is a block diagram showing a microparticle measurement system according to an embodiment.

FIG. 6 is a block diagram showing a microparticle measurement system 1A according to an embodiment. The nanopore device 100 is represented as a parallel connection circuit including a resistor Rp1 and a capacitor Cp1 coupled in parallel. The measurement apparatus 200A is provided with an additional resistor or an additional capacitor so as to absorb the change in the product of Rp1 and Cp1 involved in the nanopore device 100.

The transimpedance amplifier 210A includes an amplifier 212, capacitors Cf1 and Cf2, and resistors Rf1 and Rf2. The inverting input terminal of the amplifier 212 is coupled to the electrode 106 of the nanopore device 100. A reference voltage is applied to the non-inverting input terminal of the amplifier 212. The reference voltage may be a ground voltage. Also, other voltages may be employed as the reference voltage.

The first resistor Rf1 and the second resistor Rf2 are coupled in series between the output terminal and the inverting input terminal of the amplifier 212. The first capacitor Cf1 is coupled in parallel with the first resistor Rf1. The second capacitor Cf2 is coupled to the output of the amplifier 212. The first capacitor Cf1 is a capacitor explicitly and intentionally provided, which differs from a parasitic capacitance that occurs due to the first resistor Rf1.

A calibration controller 250A is capable of changing a circuit constant of the measurement apparatus 200A according to the control data received from the data processing apparatus 300. In this example, description will be made assuming that the data processing apparatus 300 performs the optimization of the circuit constant in the calibration mode, and the final circuit constant is transmitted from the data processing apparatus 300 to the interface 240.

In the example shown in FIG. 6, the second resistor Rf2 is configured as a variable resistor that provides an adjustable circuit constant. A resistance control unit 252 and a decoder 254 of the calibration controller 250 set the resistance value of the second resistor Rf2 according to a control instruction received from the data processing apparatus 300. As the second resistor Rf2, a digital potentiometer may be employed.

The amplifier 212 is designed employing a variable gain feedback method. Such an amplifier provides a higher operation speed as compared with typical transimpedance amplifiers. Furthermore, such an amplifier supports control of the bandwidth. The gain of the amplifier 212 will be represented by "G". The gain G can be employed as a circuit constant that can be changed. The gain G obtained in the calibration operation of the data processing apparatus 300 is set for the amplifier 212 by means of the gain control unit 256 and the decoder 258.

The measurement apparatus 200A may further include a third capacitor Cp2 and a third resistor Rp2. At least one from among Cp2 and Rp2 may be employed as an adjustable circuit constant. In this example, the third resistor Rp2 is configured as a variable resistor such as a digital potentiometer or the like. A resistance value determined by the data processing apparatus 300 is set for the third resistor Rp2 by means of a resistance control unit 260 and a decoder 262.

The voltage source 220 includes a waveform generator 222, a D/A converter 224, and a driver 226. In the calibration mode, the waveform generator 222 generates waveform data of the calibration voltage Vcal(t). The D/A converter 224 converts the waveform data into an analog waveform signal. The driver 226 receives the output of the D/A converter 224, and applies the calibration voltage Vcal(t) across the electrode pair 106 and 108.

Figure 7:
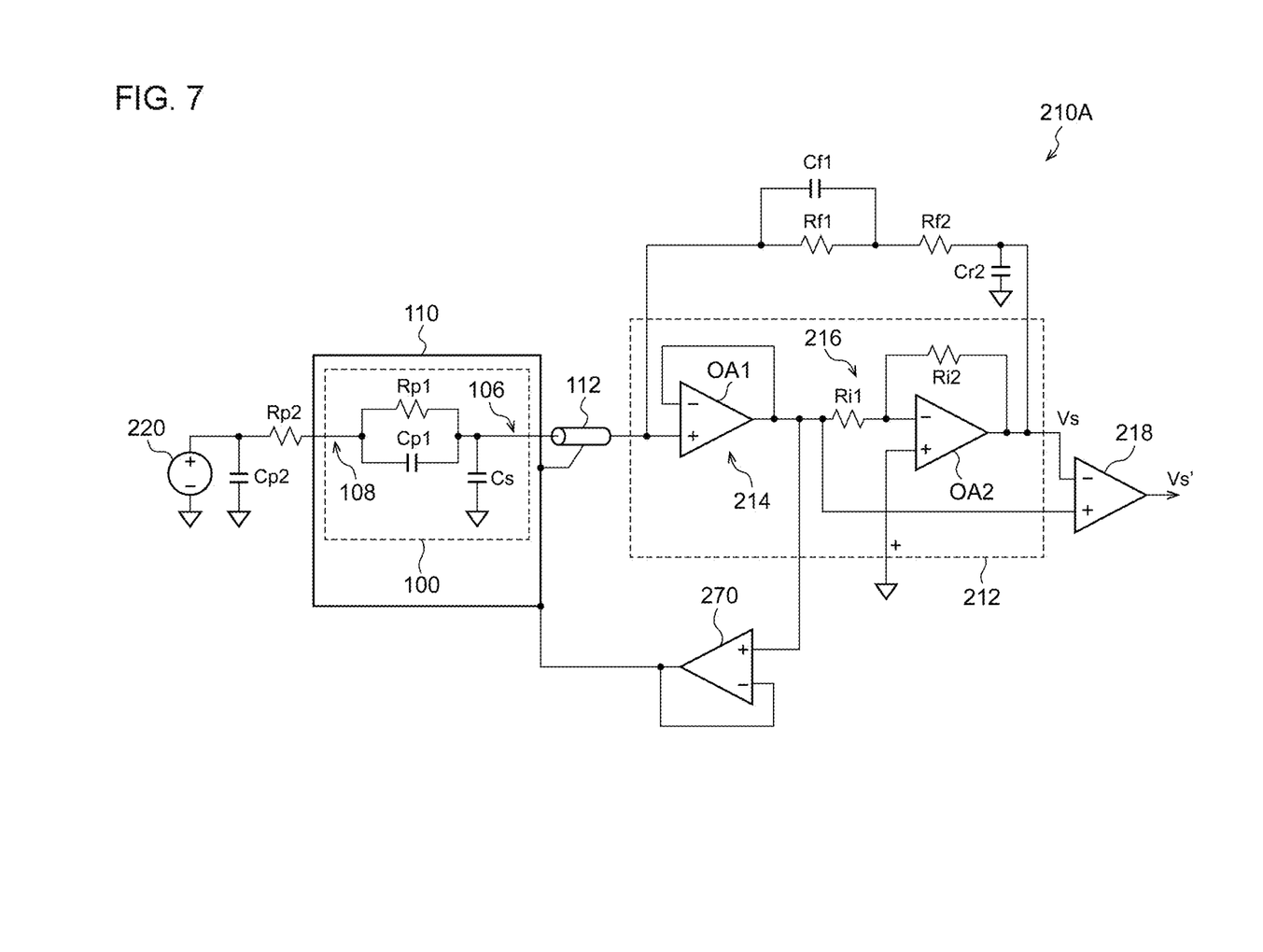
FIG. 7 is a circuit diagram showing an example configuration of an amplifier.

FIG. 7 is a circuit diagram showing an example configuration of the amplifier 212. Operational amplifiers commercialized for microscopic current measurement are configured using a FET (Field Effect Transistor) or JFET (Junction Field Effect Transistor) in order to suppress the input bias current such that it is maintained at a low level. However, such operational amplifiers have a tradeoff disadvantage of a narrow bandwidth as compared with high-speed operational amplifiers such as a Bi-CMOS or the like. In order to solve this problem, the amplifier 212 has a multi-stage structure including two or more operational amplifiers. As the first stage, an operational amplifier for microscopic current measurement is employed. Furthermore, as the second and subsequent amplifiers, a high-speed amplifier is employed. This arrangement is capable of supporting a wide bandwidth as compared with a transimpedance configured as a single amplifier.

Specifically, the amplifier 212 includes a first operational amplifier OA1, a second operational amplifier OA2, and resistors Ri1 and Ri2. The first operational amplifier OA1 configured as the first stage is configured as a FET or a JFET. The second operational amplifier OA2 and the differential amplifier 218 are each configured as a high-speed amplifier configured as a Bi-CMOS.

The first operational amplifier OA1 configured as the first stage forms a voltage follower. The second operational amplifier OA2 and the resistors Ri1 and Ri2 form an inverting amplifier 216. The non-inverting input terminal of the second operational amplifier OA2 corresponds to the non-inverting input terminal of the amplifier 212 shown in FIG. 6. The output of the second operational amplifier OA2 corresponds to the output terminal of the amplifier 212 shown in FIG. 6. The gain of the amplifier 212 can be regarded as the gain of the inverting amplifier 216, which is represented by G=Ri2/Ri1. Accordingly, in a case in which the gain G is to be configured as a variable gain, at least one from among the resistors Ri1 and Ri2 may preferably be configured as a variable resistor.

As a latter stage of the amplifier 212, a differential amplifier (subtractor) 218 is provided. The differential amplifier 218 receives the output of the voltage follower 214 configured as the first stage and the output of the inverting amplifier 216 configured as the second stage, and outputs the difference between them as a voltage signal Vs'. By employing the differential amplifier 218, this arrangement is capable of removing common mode noise that occurs in the first-stage operational amplifier OA1 and the second-stage operational amplifier OA2.

The nanopore device 100 is shielded by a metal shield casing 110. A guard amplifier 270 outputs a signal having the same electric potential as that of the electrode 106 as a driving guard signal, and applies the driving guard signal to the shield casing 110. This provides shielding from the effects of noise. Also, the electrode 106 and the amplifier 212 may be coupled via a coaxial cable 112, and an external conductor of the coaxial cable 112 may be driven by the guard amplifier 270. This allows the effects of the parasitic capacitance Cs that occurs between the electrode 106 and the ground to be minimized, thereby improving distortion of the signal and improving the bandwidth of the amplifier.

Next, description will be made regarding the calibration of the microparticle measurement system 1A. The capacitor Cf1 provided as an additional capacitor to the transimpedance amplifier 210A is designed to have a large capacitance in order to provide a balance with the RC product on the nanopore device 100 side.

Furthermore, by providing the resistor Rf2 and the capacitor Cf2 as additional components, and by adjusting the circuit constant so as to satisfy the relation Rf1×Cf1=Rf2×Cf2, this arrangement is capable of virtually canceling out the capacitor Cf1 from the viewpoint of the transfer function of the feedback circuit. This arrangement dramatically widens the bandwidth as compared with a circuit in which only the parasitic capacitance of the resistor Rf1 exists.

Furthermore, as shown in FIG. 7, in a case in which the amplifier 212 is designed to have a multi-stage configuration with the resistor Rf1 having a resistance value of 100 MΩ in order to raise the internal gain, this arrangement is capable of supporting a 1-MHz bandwidth. By configuring the resistor Rf2 as a variable resistor such as a digital potentiometer or the like, this arrangement is capable of eliminating the effects of uncertain factors such as parasitic capacitances etc.

Furthermore, by providing the resistor Rp2 and the capacitor Cp2 as additional components on the nanopore device 100 side such that they are arranged between the voltage source 220 and the nanopore device 100, and by adjusting the circuit constant by adjusting the product (Rp1×Cp1), which is a variable value, so as to satisfy the relation Rp1×Cp1=Rp2×Cp2, this arrangement is capable of canceling out the capacitor Cp1 as viewed from the amplifier side.

By providing this function, this arrangement allows the transimpedance amplifier 210A to have a maximized bandwidth, and supports stable operation of the nanopore device 100 with respect to which there are many uncertain factors.

Furthermore, by employing a digital potentiometer as the variable resistor, and by controlling the variable resistor in an online manner, this arrangement provides improved usability.

First Modification

Description has been made with reference to FIG. 7 regarding an arrangement in which the amplifier 212 is configured as a two-stage configuration. Also, other multi-stage configurations employing a negative feedback operation and having three, four, or more amplifier stages may be employed.

Second Modification

Description has been made with reference to FIG. 7 regarding an arrangement in which the first-stage amplifier is configured as a voltage follower having a gain g=1. However, the present invention is not restricted to such an arrangement. Also, the gain g may be designed to be larger than 1. In this case, the guard amplifier 270 may preferably be configured as an amplifier having a gain of 1/g.

Third Modification

Description has been made in the embodiment regarding an arrangement in which, as each of the several variable resistors, a potentiometer that can be digitally controlled is employed. Also, a part or all of them may each be configured as a manually controlled variable resistor. In this case, the corresponding resistance value may be adjusted manually by the user based on the voltage waveform measured as the calibration voltage waveform.

Fourth Modification

With such an arrangement shown in FIG. 7, in a case in which the effects of the capacitance Cs coupled to the ground are negligible, a driving guard (270, 110) may be omitted.

Fifth Modification

With such an arrangement shown in FIG. 7, in a case in which the effects of common mode noise that occurs in the two operational amplifiers OA1 and OA2 are negligible, the last-stage differential amplifier 218 may be omitted.

Sixth Modification

The combinations of the adjustable circuit constants have been described in the embodiment for exemplary purposes only. Also, desired combinations thereof may be employed. Also, other circuit constants that differ from those as described above for exemplary purposes may be configured as adjustable circuit constants.

Seventh Modification

Description has been made in the present specification regarding a microparticle measurement apparatus. However, the present invention is not restricted to such an application.

Also, the present invention is widely applicable to various kinds of measurement devices that support microcurrent measurement using a nanopore device, examples of which include DNA sequencers.

Eighth Modification

Description has been made in the embodiment regarding an arrangement in which a rectangular wave is employed as the calibration voltage Vcal. However, the present invention is not restricted to such an arrangement. Also, as the calibration voltage Vcal, a multitone signal, a swept sine wave signal, an impulse signal, etc. may be employed.

While the preferred embodiments of the present invention have been described using specific terms, such description is for illustrative purposes only, and it is to be understood that changes and variations may be made without departing from the spirit or scope of the appended claims.

What is claimed is:

1. A measurement apparatus structured to measure a current signal that flows through a nanopore device having an aperture and an electrode pair, the measurement apparatus comprising:
    a transimpedance amplifier structured to convert the current signal into a voltage signal; and
    a voltage source structured to apply a DC bias voltage across the electrode pair in a normal measurement operation mode, and to apply a calibration voltage including an AC component across the electrode pair in a calibration mode,
    wherein, in the normal measurement operation mode, the nanopore device includes particles to be detected,
    and wherein in the calibration mode, the nanopore device does not include particles to be detected and at least one circuit constant of the measurement apparatus can be calibrated based on an output signal of the transimpedance amplifier and the calibration voltage.

2. The measurement apparatus according to claim 1, wherein the calibration voltage has a rectangular waveform.

3. The measurement apparatus according to claim 1, wherein at least one circuit constant described above is adjustable such that a waveform of the output signal of the transimpedance amplifier approaches a waveform of the calibration voltage.

4. The measurement apparatus according to claim 1, wherein at least one circuit constant described above is adjustable such that a transfer function defined with a waveform of the calibration voltage as an input thereof, and with an output signal of the transimpedance amplifier as an output thereof, approaches an ideal characteristic function.

5. The measurement apparatus according to claim 1, wherein the transimpedance amplifier comprises:
    an amplifier arranged such that an inverting input terminal thereof is coupled to a first electrode of the electrode pair and a non-inverting input terminal thereof receives a reference voltage;
    a first resistor and a second resistor coupled in series between the inverting input terminal of the amplifier and an output terminal of the amplifier;
    a first capacitor arranged in parallel with the first resistor; and
    a second capacitor coupled to the output terminal of the amplifier.

6. The measurement apparatus according to claim 5, wherein at least one from among a resistance value of the second resistor and a capacitance value of the second capacitor is a variable value.

7. The measurement apparatus according to claim 5, wherein the amplifier is structured to have a variable gain.

8. The measurement apparatus according to claim 5, wherein at least one from among the first resistor and the first resistor is structured so as to be variable.

9. The measurement apparatus according to claim 1, further comprising a resistor and a capacitor arranged between the voltage source and a second electrode of the electrode pair.

10. The measurement apparatus according to claim 9, wherein a time constant provided by the resistor and the capacitor is adjustable.

11. The measurement apparatus according to claim 1, further comprising:
    a digitizer structured to convert an output voltage of the transimpedance amplifier into digital data; and
    an interface structured to transmit an output of the digitizer externally.

12. A microparticle measurement system comprising:
    the measurement apparatus according to claim 11; and
    a data processing apparatus coupled to the interface of the measurement apparatus.

13. The microparticle measurement system according to claim 12, wherein at least a part of an operation for correcting at least one circuit constant of the measurement apparatus is executed by the data processing apparatus.

* * * * *